US007455405B2

(12) United States Patent
Victor et al.

(10) Patent No.: US 7,455,405 B2
(45) Date of Patent: Nov. 25, 2008

(54) METHOD AND SYSTEM FOR PERCEPTUAL SUITABILITY TEST OF A DRIVER

(75) Inventors: Trent Victor, Gothenburg (SE); Petter Larsson, Ytterby (SE)

(73) Assignee: Volvo technology Corporation, Gothenburg ( * ) Notice: Subject to any disclaimer, the term of this patent is extended or adjusted under 35 U.S.C. 154(b) by 0 days.

(21) Appl. No.: 11/534,555

(22) Filed: Sep. 22, 2006

(65) Prior Publication Data

US 2007/0132950 A1 Jun. 14, 2007

Related U.S. Application Data

(63) Continuation of application No. PCT/EP2005/000305, filed on Mar. 22, 2005, and a continuation of application No. PCT/EP2004/003009, filed on Mar. 22, 2004.

(51) Int. Cl.
*A61B 3/00* (2006.01)
(52) U.S. Cl. ........................ 351/200; 351/201; 351/202; 351/209
(58) Field of Classification Search .................. 351/200
See application file for complete search history.

(56) References Cited

U.S. PATENT DOCUMENTS

| | | | | |
|---|---|---|---|---|
| 4,889,422 A | * | 12/1989 | Pavlidis | ...................... 351/210 |
| 5,422,690 A | * | 6/1995 | Rothberg et al. | ............ 351/209 |
| 5,942,954 A | * | 8/1999 | Galiana et al. | .............. 351/209 |
| 2002/0188219 A1 | | 12/2002 | Suchard | |
| 2004/0252277 A1 | * | 12/2004 | Chmielewski et al. | ...... 351/209 |

FOREIGN PATENT DOCUMENTS

| | | |
|---|---|---|
| DE | 3803916 A1 | 8/1989 |
| WO | 9746158 A1 | 12/1997 |

OTHER PUBLICATIONS

International Search Report for International Patent Application PCT/EP2005/03053, dated Aug. 18, 2005.
International Search Report for International Patent Application PCT/EP2004/03009, dated Nov. 9, 2004.
Rodriguez; et al., "Estimation of BAC from the Analysis of Nystagmus", Annual international Conference of the IEEE Engineering in Medicine and Biology Society, 1990, vol. 12, No. 2, College Station.

* cited by examiner

*Primary Examiner*—Jessica T Stultz
(74) *Attorney, Agent, or Firm*—Novak Druce + Quigg, LLP

(57) ABSTRACT

A tractor truck configured for towing trailers of different air connection configuration. The truck has a first and a second tractor protection valve, each configured to be located on the tractor at a location remote from the other. Each tractor protection valve location is proximate a typical position at which a mating connection on a trailer will be located when hitched to the tractor. The truck also has a selector which is operator-transitionable between a first configuration in which the first tractor protection valve is activated to supply pressured air to an interconnected trailer and a second configuration in which the second tractor protection valve is activated to supply pressured air to a different interconnected trailer.

24 Claims, 4 Drawing Sheets

METHOD AND SYSTEM FOR PERCEPTUAL SUITABILITY TEST OF A DRIVER

CROSS-REFERENCE TO RELATED APPLICATIONS

The present application is a continuation patent application of International Application No. PCT/EP2005/0003053 filed 22 Mar. 2005 which is published in English pursuant to Article 21(2) of the Patent Cooperation Treaty and which claims priority to International Application No. PCT/EP2004/003009 filed 22 Mar. 2004. Said applications are expressly incorporated herein by reference in their entireties.

FIELD

The invention relates to methods and systems for conducting Perceptual Suitability Tests (PST) for a driver and/or any other person who operates equipment, and/or devices such as a vehicle, a train, an aircraft, a ship, a nuclear reactor, a plant, a chemical process, etc. The invention is especially provided for enabling and disabling Perceptual Impairment Ignition Interlock Devices (PERCEPTIIID) for such vehicles, equipment, and/or devices, the operation of which could especially pose a general and/or potential risk for the environment and/or other people. This invention is also relevant for situations other than driving, but the examples here will be given for driving.

BACKGROUND

Perceptual errors are reported to cause an estimated 80% of all highway accidents (Treat et al, 1977). Inattention is reported to be the leading cause of collisions (Wang et al, 1996), and late detection of traffic conflicts is a basic driver error (Rumar, 1990). There is an enormous cost to society from accidents and errors attributed to the influence of alcohol, illegal and prescription drugs, medical conditions, or other disabling infirmity during the operation of equipment such as vehicles, trains, aircraft, ships, nuclear reactors, chemical processes, etc.

The International Council on Alcohol, Drugs, and Traffic Safety (ICADTS) provides overviews of the problems associated with alcohol, illegal drugs, and driving, especially in the following references:

(1) ICADTS Working Group on Alcohol Ignition Interlocks: Alcohol Ignition Interlock Devices I: Position Paper (2001), ISBN: 90-802908-4-x (reference is made especially to page 11, last paragraph to page 12, last paragraph);

(2) ICADTS Working Group on Illegal Drugs and Driving: Working Group Report: Illegal Drugs and Driving (2000), ISBN: 90-802908-2-3;

(3) ICADTS Working Group on Prescribing and Dispensing Guidelines for Medicinal Drugs affecting Driving Performance: Prescribing and Dispensing Guidelines for Medicinal Drugs Affecting Driving Performance (2001), ISBN 90-802908-3-1.

Especially regarding the influence of drugs and alcohol on perception and eye movements, reference is made to:

(4) Page, T. E. (1998): The Drug Recognition Expert (DRE) Response to the Drug Impaired Driver: An Overview of the DRE Program, Officer, and Procedures. Los Angeles Police Department (http://www.ci.la.ca.us/LAPD/traffic/dre/drgdrvr.htm);

(5) Leigh, R. J. and Zee, D. S.: The Neurology of Eye Movements, third edition, Oxford University Press (1999);

(6) Adler, E. V. and Burns, M. (1994) Drug Recognition Expert (DRE) Validation Study. Final report to Governor's office of Highway Safety, State of Arizona;

(7) Bigelow, G. E., et al., (1984) Identifying Types of Drug Intoxication: Laboratory Evaluation of a Subject Examination Procedure. NHTSA, DOT HS 806 753 (1985).

References (4) and (5) as well as other research show that numerous drugs—here the meaning of drug includes alcohol, prescription drugs and illegal drugs—including Central Nervous System Depressants, Inhalants, and Phenocyclidine (PCP) affect perception and eye movements. Effects on eye movement include horizontal and vertical gaze nystagmus (an involuntary but visible jerking of the eyeballs while gazing at an object), vergence deterioration, changes in pupil size, and blank staring (see references (4) and (5)). Interestingly, a test for horizontal gaze nystagmus was shown to be the best indicator of alcohol use (reference (4)). In reference (5), pages 561-564, numerous effects on eye movement by drugs are listed and references for these findings are provided. Other effects include difficulty remembering and following instructions, reduced ability to divide attention, sensory-motor coordination deterioration, and/or changes in pupil size. (Some of these difficulties, especially sensory-motor coordination and reaction time, have been exploited by similar ignition interlock patents.) Various types of nystagmus can be caused by various medical conditions.

In reference (4), an overview of the Drug Recognition Expert (DRE) program and the Drug Evaluation and Classification Program (DECP) is provided. The DRE program was started by the Los Angeles Police Department (LAPD) and developed in a body of research (e.g. references (6) and (7)). The original need for the DRE method was driven partially because the blood alcohol content (BAC) breath test results can be below the statutory level, yet the person can appear to be inexplicably impaired by drugs. The DRE uses a drug categorization system with seven categories with numerous drugs per category. The overall effects within each category are the same. The categories are: 1. Central Nervous System Depressants, 2. Inhalants, 3. Phencyclidine (PCP), 4. Cannabis, 5. Central Nervous System Stimulants, 6. Hallucinogens, 7. Narcotic Analgesics. An additional category, "Poly-drug Use," is used when multiple drugs are used.

In addition to drugs, eye movement and perception can be influenced by a number of medical conditions or crises such as stroke, epilepsy, multiple sclerosis, uncontrolled diabetes, etc. and other operator states. Regarding such influences, it has to be considered that they produce effects that are similar to drug impairment (reference (4)). Reference is made to US Patent Application Publication 2001/0028309A1, paragraphs 79-82, disclosing a number of such examples for medical, psychological, and activity situations.

Furthermore, reference is made to the following documents: U.S. Pat. No. 3,780,311; U.S. Pat. No. 4,901,058; U.S. Pat. No. 4,912,458; U.S. Pat. No. 3,665,447; WO 87/07724; U.S. 2003/0037064A1; U.S. Pat. No. 4,983,125; U.S. Pat. No. 3,755,776; U.S. Pat. No. 3,886,540; U.S. Pat. No. 6,229,908 and U.S. Pat. No. 3,735,381.

In general, most of these documents refer to ignition interlock or similar devices that require the driver of a vehicle to execute some type of test before he can start the vehicle. However, it is considered detrimental that the driver actively has to execute such tests. Furthermore, the disclosed impairment measurements have several other disadvantages.

SUMMARY

Accordingly, it is a general object of the invention to provide a method and system for automatically executing a suitability test with respect to perceptual impairment of a driver or any other person who operates equipment and/or a device such as a vehicle, a train, an aircraft, a ship, a nuclear reactor, a plant, a chemical process, and the like.

Furthermore, it is an object of the invention to provide a method and system for automatically executing a drug recognition expert (DRE) on a driver or any other person involved in the operation of the above-mentioned equipment and/or device. It is another object of the invention to provide a method and system for automatically executing a suitability test with respect to perceptual impairment of a driver or any other person involved in the operation of the above-mentioned equipment and/or devices, in connection with at least one of medical conditions or crises such as stroke, epilepsy, multiple sclerosis, uncontrolled diabetes, etc. and other operator states.

It is another object of the invention to provide a method and system for automatically testing for the influence of drugs and/or alcohol and/or medical conditions or crises such as stroke, epilepsy, multiple sclerosis, uncontrolled diabetes, etc. and other such states on perceptual suitability or impairment of a driver or any other person involved in the operation of the above-mentioned equipment and/or devices.

Furthermore, it is an object of the invention to provide a method and system that could automatically function as an ignition interlock device of a vehicle (or any other equipment and/or device as mentioned above) in case a certain level of perceptual suitability of a driver (or any other person operating equipment and/or a device) is not detected.

It is another object of the invention to provide a method and system for automatically conducting such perceptual suitability tests on a driver of a vehicle or a person operating equipment or a device while driving a vehicle or operating the equipment or device, respectively.

Finally, it is an object of the invention to provide a method and system for automatically executing such suitability tests on the basis of eye and/or head movements or reactions of the related vehicle driver or any other person who operates equipment and/or devices as mentioned above.

BRIEF DESCRIPTION OF THE DRAWINGS

Further details, features, and advantages of the invention will be apparent from the following description of exemplary embodiments of the invention in connection with the drawings, in which.

DETAILED DESCRIPTION

Figure 1:
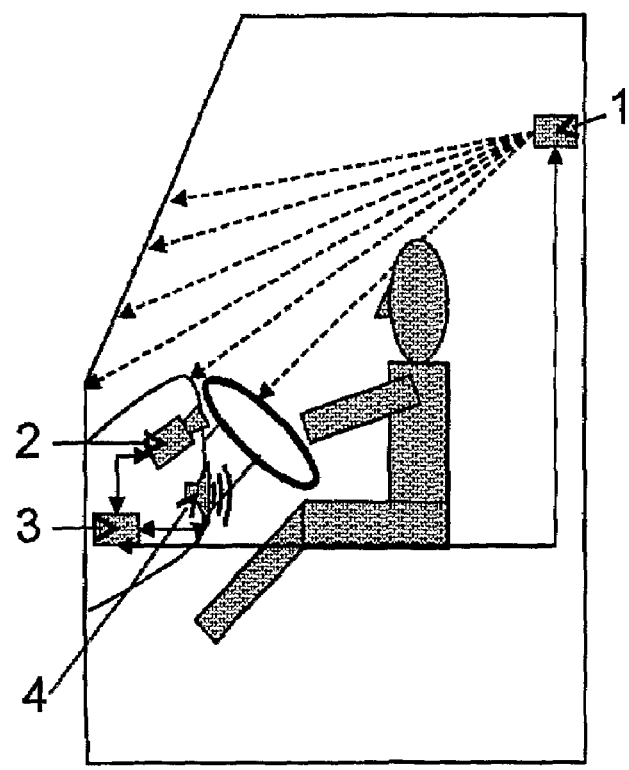
FIG. 1 illustrates basic components of a preferred embodiment of a system according to the invention.

A system according to the invention shall be described exemplarily in the form of a safety apparatus for preventing a person under the influence of alcohol, drugs, or other disabling infirmity from starting or operating potentially dangerous equipment such as an automobile or vehicle. The apparatus inhibits vehicle operation until the operator has performed a perceptual suitability test. For example, the test results and/or bypass events can simply be logged on the tachograph, driver smart card, fleet management system, or be transmitted back to the office by some type of communication, e.g. GPRS or GSM data. Apparatus according to the invention also tests for similar impairment continuously once the vehicle or equipment is in use. The apparatus could also be used as a portable device, e.g., to be used by police for examination of suspected drug users for example.

A basic idea is to assess the perceptual suitability of an operator to perform a task such as driving. Perceptual ability is influenced by alcohol, drugs, and medical conditions, but also by other factors such as age and experience. Thus, a subject of the invention is to test for the perceptual effects of alcohol, drugs, etc., but not for the presence of alcohol, drugs, etc. per se. This is particularly important because, e.g., a particular concentration of a drug can have quite different effects on different people and/or under different circumstances. The effects of any drug depend on a number of additional factors such as dose, user tolerance, metabolism, how the drug was administered, the drug's purity, the user's expectations, coexisting illness, fatigue, and the presence of other drugs or substances.

This invention uses accepted medical techniques in order to detect the well-established effects of the drugs of abuse. It proposes to combine the detection of known effects of drugs and alcohol (see, e.g., in reference (5) above) with both new and known assessment procedures. Parts of the DRE method could be made automatic, and new complementary stimuli from other research could be used together with new stimuli and methods. It does so with a novel combination of technology. The use of this technology is similar to how the Blood Alcohol Ignition Interlock Device is used (see reference (1), especially between page 11, last paragraph and page 12, last paragraph, which is incorporated by reference) and similar to how other ignition interlock devices are used (according to at least one of the above-mentioned U.S. patents).

Background Information on Eye Movements:

Eye movements can be categorized into two basic categories: fast phase and slow phase eye movements. Saccades are fast phase eye movements, while fixations, smooth pursuits, vergence, and the vestibulo-ocular-reflex are slow phase eye movements. The following definitions are taken from Carpenter, R. H. S., 1998, Movements of the Eyes, 2nd Edition. Pion: London.

Fixations are defined as pauses over informative regions where the eyes can assimilate information. To be a valid fixation, the pause has to last for at least some 150 ms, the time the brain needs to utilize the information. Although it is referred to as a "fixation," the eyes still move, making micromovements like drift (typically in the range of 4 degrees per second), tremor (typically in the range of 20-40 degrees per second), and micro-saccades (typically in the range of 200 degrees per second) while "fixed" on an object or area. These small movements are of very low amplitude, or very slow, and are part of what defines a fixation.

Smooth pursuits are a subcategory of a fixation; that is, a fixation on a moving target or a fixation on a stationary (or moving) object while the observer is in motion. When we track a target, the eyes first use saccades to bring the fovea onto the target, then slower, continuous movements are performed that track the target and are dependent upon the speed of the target. The slow continuous movements with velocities ranging between 80 and 160 degrees per second constitute smooth pursuits. Importantly, smooth tracking movements or smooth pursuits cannot occur at will in the absence of a smoothly moving target. That is, we need a smoothly moving target to be able to perform a smooth pursuit. Efforts to voluntarily perform smooth pursuits within a stationary visual field result in a sequence of saccades. Thus, smooth pursuits are a sensorimotor reflex, operating under the control of the stimulus rather than free will which is different from saccades.

Saccades are rapid eye movements that occur as a person's gaze changes between two points. Saccadic movement varies in amplitude, duration, velocity, and direction. The duration of saccades larger than about five degrees visual angle in amplitude are about 20-30 ms; thereafter, two milliseconds can be added for every additional degree. Peak velocities typically range from some 10 degrees per second for amplitudes less than 0.1 degrees to more than 700 degrees per second for large amplitudes. Further, saccades do not follow a target as smooth pursuit movements do. Thus, WO 2004/034905A1 discloses using stimulus to elicit and test saccadic eye movements and not smooth pursuit movements.

FIG. 1 shows a side view into the cabin of a vehicle in which a driver is sitting and an exemplary and preferred embodiment of a system according to the invention which is installed within the cabin. This system comprises a stimulus generation device 1; an eye movement and/or head movement and/or pupil reaction registration device 2; a computation, control, and output device 3; and a sound generation unit 4.

Figure 2:
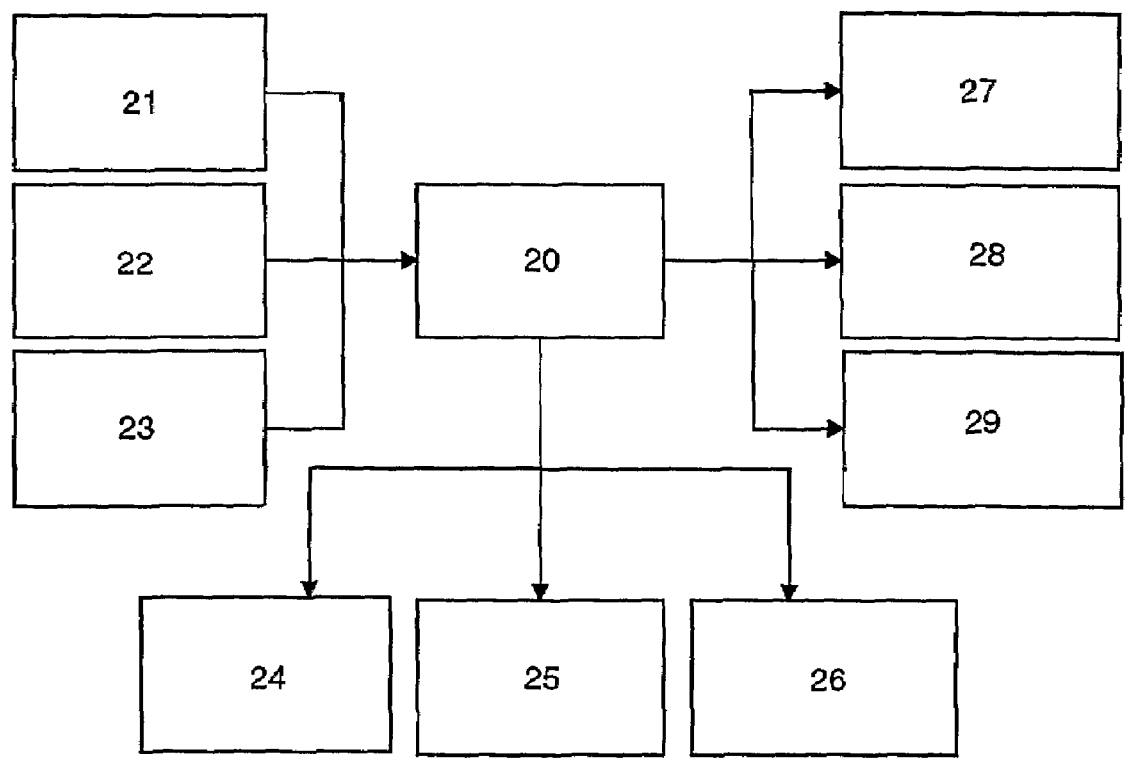
FIG. 2 is a schematic block diagram of an exemplary embodiment of a system according to the invention.

FIG. 2 shows a schematic block diagram of a more detailed and alternative structure of a system according to the invention. The system comprises a computation and control unit 20 which is connected for receiving input signals from one or more cameras 21, from a status display 22, and from manual controls 23. The computation and control unit 20 generates output signals for controlling, for example, a vehicle ignition device 24, a tachograph 25, and/or communication devices 26. Furthermore, the computation and control unit 20 generates output signals for controlling a visual stimuli generation device 27, one or more eye illuminators 28, and/or a sound generation device 29.

Corresponding with the structure shown in FIG. 1, the stimulus generation device 1 preferably comprises units 27 and 28; the registration device 2 preferably comprises unit 21; and the computation, control, and output device 3 preferably comprises unit 20. The sound generation unit 4 corresponds with unit 29.

Stimulus Generation Device 1:

An example of a stimulus generation device 1 includes a commercially available diode laser (see www.lasershow.se), which is capable of producing color picture stimuli as known in the prior art. A picture stimulus is made up of a single laser beam which is moved around so quickly that the impression of an image is made. The beam is controlled by two small electromagnetic motors x- and y-axis) with a small mirror on the motor axis. A number of different lasers are practical, including red, blue, or green lasers. A simple, inexpensive laser such as those commonly used as pointing devices for presentations before a group of people can be used. An automotive grade laser would be used in a final product. Other stimulus generation devices such as conventional computer displays and light emitting diodes (LEDs) could be used in front of the driver. Any light source, even a common flashlight (especially a high intensity LED style flashlight) could be used.

Another example of a stimulus generation device 1 could be a computer projector such as those used for presentations at conferences, for example those made by Barco. This type of projector could become smaller, less expensive, and automotive grade in the future.

Furthermore, a transparent and selectively reflectant film could be applied to all or sections of the windshield for projecting the optical stimulus by the stimulus generation device 1 onto it. The film could be selected to specifically reflect specific wavelengths which are most appropriate for the invention.

Eye illuminators mounted on the dashboard are preferably used to illuminate the face of the driver for improved eye tracking registration performance and, for example, to create brief flashes of light that the pupil reacts to. An example of calculation of pupil reaction is described in U.S. Pat. No. 5,422,690. However, a main difference from this U.S. Pat. No. 5,422,690 is that according to the invention the pupil reaction to a light stimulus is detected with a remotely mounted camera as described below.

The stimulus generation device 1 does not necessarily have to be calibrated to the interior of the vehicle. However, calibration may allow the laser to be used to point to particular things in the interior. For example, the laser could point to buttons that the driver should press.

Eye/Head Movement/Pupil Reaction Registration Device 2:

The registration device 2 could utilize one of many commercially available eye and head tracking sensors, such as FaceLAB from Seeing Machines (see www.seeing-machines.com) or devices from Tobii Technology, Smarteye, SensoriMotoric Instruments, Siemens, Applied Science Laboratories, Delphi, etc. The eye and head tracking device would have to meet the accuracy requirements determined by the spatiotemporal characteristics of the eye movements being classified. Relevant eye and head measures include but are not limited to pitch and yaw gaze angles for one or both eyes; mean pitch and yaw gaze angles for one or both eyes; head position in three dimensions; head direction in three dimensions; eyelid closure; and pupil size. Other examples of eye movement registration devices 2 that could be applied include eyeglass or head mounted versions of eyetrackers (of which the US patent application publication US2001/0028309A1 (Torch) discloses one of many other examples). A preferred embodiment according to the invention uses an automotive grade eye movement sensor with high image resolution and ambient light measurement.

Substantially two problems have to be considered in connection with remotely mounted eye movement registration devices 2. First, with any camera, image details of the eye become poorer as the distance between the eye and the camera increases. Because the camera is mounted remotely, e.g. in or on the dashboard of a vehicle, and not close to the eye, loss of image detail can be compensated with either higher resolution cameras or more robust detection algorithms. According to the invention, preferably both high resolution cameras and robust detection algorithms are used. Modern and future high resolution cameras are capable of providing an image detail comparable to that described in U.S. Pat. No. 5,422,690 even though the cameras are mounted much further away from the driver. Furthermore, a remote camera mounted on two servos (to control the camera direction in the x- and y-directions) with a zooming lens can actively follow the moving head of the driver or operator. Computer vision software then preferably stabilizes the zoomed-in eye image and makes high quality measurements as a result of the high resolution provided over the eye.

The second problem caused by a remote setup that especially affects detection of pupil reaction is that of ambient light. U.S. Pat. No. 5,422,690 and similar references such as US2002/0188219A1 disclose a setup where the eye is shielded from ambient light, thus creating a dark environment as a starting point for pupil reaction. The pupil's resting state in a dark environment is very dilated, and a brief flash of light therefore creates a larger reaction than if, for example, the resting state is in daylight. To test the pupil reaction in ambient light conditions, an ambient light measurement is needed and an algorithm that adapts to ambient lighting conditions is needed. Measurement of ambient light is possible through light measurement by the camera sensor or by a phototransistor mounted near the driver's face. Signal-to-noise ratio also is highest in dark conditions and decreases as a function of ambient light. With decreasing signal-to-noise ratio, detection becomes more difficult, but correct classification of large enough effects is still possible as long as ambient light measurement is made.

Computation, Control and Output Device 3:

The computation, control, and output device 3 preferably comprises commercially available electronic components including functions and software programs for:

a) controlling the stimulus generated by means of the stimulus generation device 1, b) classification of the eye/head movement/pupil reaction data detected by the eye/head movement/pupil reaction registration device 2;

c) perceptual impairment decision making; and d) output runs on the computation, control, and output device 3.

These components and functions shall be described in more details in the following:

a) Controlling the stimulus generated by means of the stimulus generation device 1 (stimulus generation) is explained for each elicited eye movement (or ocular) performance indicator further below.

b) The classification of the eye/head movement/pupil reaction data detected by the eye/head movement/pupil reaction registration device 2 comprises quantifying by detecting and calculating or determining one or a plurality of ocular performance indicators of a driver and then quantifying a value of perceptual suitability from the quantified indicators:

Quantification of Perceptual Suitability:

Perceptual Suitability (PS) is a function of the performance of Smooth Pursuit (SP), Pupil Reaction (PR), Head Coordination (HC), Vergence (V), Saccadic Velocity (SV), and other ocular movements (O):

$$PS = f(SP, PR, HC, V, SV, O)$$

One exemplary way to implement the PS function is:

$$PS = A^*SP + B^*PR + C^*HC + D^*V + E^*SV + F^*O, A, B, C, D, E, F \in [0, \ldots 1]$$

Other functions (such as squared parameters, roots of parameters, etc.) can also be used to implement this function depending on the purpose of the function.

The ocular indicators SP, PR, HC, V, SV, and O are quantified by detection and calculation or determination independently as described below. Each indicator ranges typically from 0 to 100 (if accordingly normalized). The PS function is the weighted sum of these indicators. The weighting factors A-F are chosen so that the combination of indicators (SP, PR, HC, V, SV, and O) results in the best quantification of perceptual suitability of a driver possible for given circumstances like, e.g., a certain installation (camera sensor, stimuli generator, cab environment, etc.) and/or environmental state (day/night, direct sunlight) and/or other conditions. The weighting factors can be negative values and/or functions as well.

The weighting factors can be tuned by several methods, including neural networks, statistical analysis of the indicators, noise content in measurements, or indicator confidence (to be calculated by noise content and measurement accuracy). In some cases, one or more factors (up to all but one of the factors) can be 0 if, e.g., an indicator does not give sufficiently accurate information and/or if the Signal-to-Noise Ratio is low and/or if a more simple or inexpensive method/system shall be realized.

The stimuli presented to the driver determine the indicator that can be sensed and evaluated at a specific moment. For example, the performance of a smooth pursuit tracking behavior can only be calculated if the stimuli present a traceable target with suitable smooth pursuit speeds and vice-versa. Certain stimuli patterns, e.g. a smooth pursuit pattern with sudden shifts of direction, can give input to several indicator calculations simultaneously, in this case performance of SP, SV, and O. Hence, indicator calculation is driven by stimuli generation.

Thus, by using the function for Perceptual Suitability as indicated above with a weighted combination of selected performance indicators, the Perceptual Suitability of a driver or operator is quantified.

The simplest method and system configuration would only use a smooth pursuit stimulus presentation and calculate the perceptual suitability PS=f (SP). Smooth pursuit (SP) can be chosen as the ocular indicator of preference for the detection of alcohol as well as a number of other drugs, see references (4), (5), and (7). Advantages of such a simple method and system configuration include shorter test time (because only smooth pursuit stimuli are to be detected and evaluated); simpler hardware (e.g. image resolution may not have to be as high because the pupil does not need to be measured and thus the camera configuration may be cheaper); simpler software (no consideration is taken of other indicators in decision making); etc.

However, the method and system becomes more sensitive and more robust as additional ones of the above-mentioned ocular indicators are added. Thus, multiple versions of the method and system are conceivable. For example, a method and system comprising a Smooth Pursuit-based calculation alone, or comprising a combined Smooth Pursuit and Pupil Reaction calculation, or comprising a combined Smooth Pursuit, Pupil Reaction, and Head Coordination calculation, etc. or a method and system using all ocular indicators can be realized.

Quantification of Smooth Pursuit (SP) Performance:

The quantification of smooth pursuit is a central aspect of this invention. Rather than attempting to segment and identify components of nystagmus, as is done in U.S. Pat. No. 6,089, 714 and Rey and Galiana, "Parametric classification of segments in ocular nystagmus," IEEE Tans. Biomed. Eng., vol. 38, (1991), pp. 142-48, smooth pursuit performance is quantified according to the invention on a scale between (and including) poor and good. Smooth pursuit performance is thus the quality of gaze stabilization on a target moving at a velocity suitable for smooth pursuit elicitation. When a driver is impaired, the gaze stability on a moving target starts to drift so that the eye cannot follow the target as well and starts to slip away from the target. As a consequence, the number of reorienting or "catch-up" saccades increases to compensate for drifts, acting to bring the fovea onto the target. Simply stated, the impaired driver cannot keep his or her eyes on a target very well. These involuntary (reflex) eye movement characteristics are evaluated by provoking them to appear.

Figure 3:
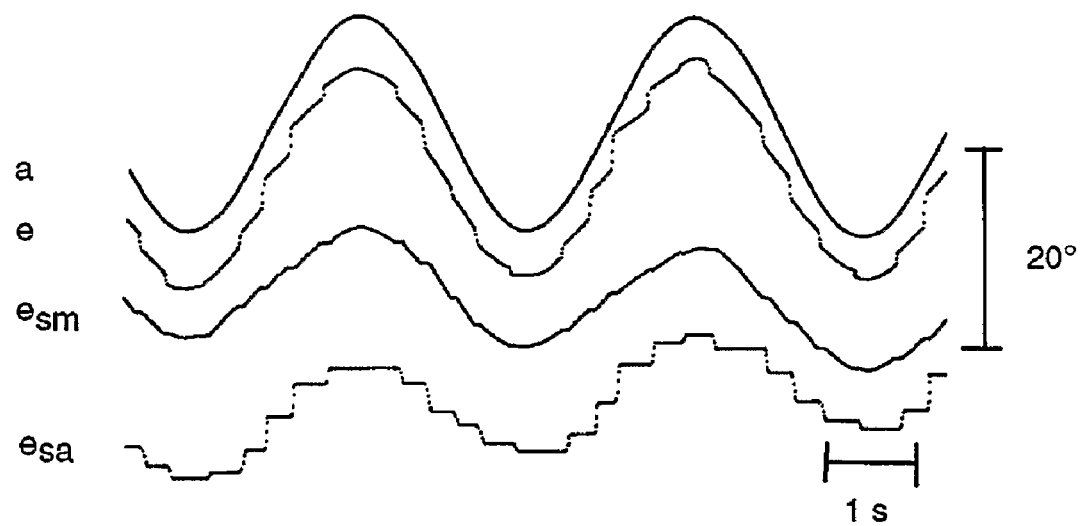
FIG. 3 shows schematic curves of eye movement components of nystagmus.

This is shown in FIG. 3 for eye movement components of nystagmus. The eyes are tracking a given pattern (curve a) which is presented to the driver. Curve (e) indicates the entire detection signal generated by means of a camera 2/21 observing the driver's eyes. This signal contains both saccade and smooth pursuits (nystagmus) of the eyes of the driver. If the saccades (curve esa) are removed from the entire signal (curve e), the resulting curve (esm) displays only the smooth tracking behavior of the eyes, which is closer to the presented ideal pattern (curve a) than the saccades (curve esa) (see Carpenter, 1988, p 55).

For determining smooth pursuit, the driver is required to follow a moving target of sub-saccadic speed with his eyes, for example a happy face 1.5 degrees visual angle in size. The target is projected by the stimulus generation device 1/27 onto the dashboard, the interior, and/or the windshield of the vehicle. One key aspect of this invention is to vary the degree of difficulty of the smooth pursuit tracking stimulus. This difficulty is comprised of two main components: target speed and target predictability. Thus, an additional key aspect of this invention is to vary the degree of predictability of the target motion that elicits smooth pursuit tracking. For example, target motion could be controlled by a mixture of three sinusoids (e.g. of 0.3, 0.6, and 1.2 Hz). By varying stimulus speed and the exact combinations of frequencies, the movement can be made more or less predictable or easy to track with the eyes. Faster speeds with more complex combinations of wave frequencies are very difficult to follow, whereas slower speeds with less complex combinations of wave frequencies are easier to follow. Another method of generating unpredictable target motion suitable for smooth pursuit testing is to generate motion of the target with a low-pass (1.25 Hz) Gaussian random process. Also, randomly stopping the stimulus, especially at high visual angles (in the periphery of the visual field) also increases tracking difficulty. Thus, it is possible to vary stimulus difficulty.

Regarding the importance of prediction in smooth pursuit eye movements and with regard to generation of randomized target motions suitable for smooth pursuit eye tracking, reference is made to Pavel, M. (1990), "Predictive control of eye movement" In E. Kowler (Ed.) Eye movements and their role in visual and cognitive processes (Elsevier).

The SP performance is a function defined by the stimuli (reference signal) and the response (measured gaze signal).

Performance($SP$)=$f$(stimuli, response)

The SP performance can be calculated (quantified) with a number of methods which can be applied with small changes for calculating other ocular indicators as well:

The angular difference or RMS value (Root Mean Square) between the reference signal and the gaze signal: The system knows the relation in position and direction of the camera and the stimulus generator. Thus, the system knows at which angle, relative to the driver's eye position and direction, stimuli are generated. The angular difference is then the relative difference between stimuli angle and gaze angle. Little difference in relative angle (or error) indicates high precision tracking of a non-impaired subject, whereas a large relative angle would indicate an impaired subject. Comparing gaze and stimuli angle instead of gaze and stimuli position makes the method robust to noise otherwise introduced by the distance to the projected stimuli. The further away a projection is made, the more noise is present in the measurement.

Pattern recognition: A neural network (NN) could be trained to recognize combinations of stimuli and responses that would indicate an impaired driver. Different NN's could be used for different characteristics, i.e., smooth pursuits and saccades.

Cross-Correlation of response and reference angles: Following the same principle as for angular difference, but cross-correlating the reference signal to obtain a measurement of how well the driver tracks the reference.

Cross-correlation can also be done between the measured eye-gaze and pre-defined curvatures of SP. This is especially useful when measuring SP in common driving behavior where the stimulus are road signs and other objects beyond the control of the system.

General Model Response: A model can describe in mathematical terms the predicted, non-impaired eye movement response to a stimulus. The stimulus is then fed both to the driver and into the model and the outputs of the two are compared. For a model tuned to respond as an unimpaired driver, a low error between the model response and the driver response indicates an unimpaired driver, whereas a high error indicates an impaired driver.

Trained Model response: This is the same as for General Model Response, however, the model is adapted to the particular driver performing the test. Adaptation could be done by recording unimpaired SPs and adjusting the model parameters to a best fit. Such information could be linked to the driver's identity via the driver's card (in the digital Tachograph) or via facial and/or iris recognition.

Timing for the above methods can be obtained from the peak correlation of target and gaze position with a cross-correlation function.

The above-described methods are also applicable to PR, HC, V, SV, and O performance calculation (quantification) with only minor changes.

Quantification of Pupil Reaction (PR) Performance:

The same procedure as is outlined in U.S. Pat. No. 5,422,690 can be used. The main difference, however, is that here the algorithm has to handle the effects of ambient light on resting pupil size as well as the interference of ambient light during the pupil reaction. These can be handled as described above.

While the driver is performing the smooth pursuit task, the target can be directed to stop at the location of the camera (to obtain the best image of the pupil) and stop momentarily. A flash of light can be administered by the eye illuminators and pupil reaction measured; thereafter, the smooth pursuit target would move on. See also "Quantification of Saccades" below for another example of how a pupil reaction-evoking stimulus can be presented.

As described above, PR has to be measured relative to ambient light, and measurement of ambient light is possible through light measurement by the camera sensor or by a phototransistor mounted near the driver's face. The measured relative PR to a suddenly emitted flash is compared to known reactions for unimpaired drivers, thus calculating a performance measure of PR.

Examples of methods to quantify performances of PR are cross-correlation, pattern recognition, General Model Response, and Trained Model Response as described above for SP.

Quantification of Vergence (V) Performance: Stimuli inducing vergence could be created by using a technique where two images are overlaid to produce a three-dimensional effect.

Examples of methods to quantify performance of V are pattern recognition, General Model Response, and Trained Model Response as described for SP.

Quantification of Saccadic velocity (SV) Performance: While the smooth pursuit testing is being performed, sudden visual events can be triggered at various visual angles to the smooth pursuit target. Sudden visual events near the target can function as distractors to the smooth pursuit tracking. Depending on the perceptual saliency of the visual distractor event, drivers will either choose to make a saccade to the visual distractor, ignore it, and/or react with their pupil. If a saccade is made, appropriate analyses of the saccadic velocity profile can be made, for example as described in U.S. Pat. No. 5,422,690. If pupil reactions are elicited, the same procedure as outlined in U.S. Pat. No. 5,422,690 can be used.

Peripheral sensitivity of a driver which is a potential indicator of peripheral impairment can be tested while driving or at stand-still. This can be tested by presenting salient stimuli that elicit an orienting reflex in the form of a saccade towards the target. Peripheral sensitivity is reduced in impaired drivers; thus, they would be less sensitive to stimuli presented in the peripheral visual field. The stimulus could be a small dot that increases in size, intensity, flickering, movement, and shape. The stimulus would be presented at increasing visual angles to detect how sensitive peripheral vision is. Reaction time to detection and hit rate (misses) give an accurate measure of impairment. Reaction time to detection could be measured by either detecting an eye movement to the stimulus or by monitoring changes in pupil size.

Examples of methods to quantify performance of SV are cross-correlation, angular difference, pattern recognition, General Model Response, and Trained Model Response as described above for SP.

Quantification of Head Coordination (HC) Performance: During the smooth pursuit tracking outlined above, the head is required to be held as still as possible. A measure of the deviation from stationary is thus desirable and indicative of impairment. The quantification of head coordination uses the same methods as outlined above for SP. In this case, the reference signal is the starting position of the head or a forward-facing model direction.

Guidance to help keep the head on target could be given by generating a sound by the sound generation unit 4 which would indicate deviation from target. For example, if the head starts to deviate from the target position, then a sound could become gradually louder as head pose and position deviates more from the desired state. Alternatively, assistance to hold the head stationary could be given by projecting a target and crosshair indicating the deviation of the head rotation or position in comparison to a target intended for the head to follow.

The head movement target could also be moving, thereby requiring the driver to follow a desired head position by listening to a sound. Driver head response to events could be required. For example, a moving stimulus dot could alternate randomly between two or three on/off temporal variations. The driver would be required to respond to these expected changes in temporal variations by moving the head in different directions.

Other Ocular Movements (O) or Performance Indicators:

Quantification of Eye Movement Gain: Eye Movement Gain is a measure of how well the eye catches up with the target. Both slow-phase targets such as those described above for Smooth Pursuit and fast-phase targets such as those described above for Saccadic Velocity can be used. Because gain can be used for quantification of both smooth pursuit targets and saccadic targets, or a combination of both, this measure is included in this section "Other ocular indicators".

Gain provides a measure of how sensitive the eye movement control system is. Gain measures the relative amplitude of gaze and target at the target's fundamental frequency. Gain is analyzed in the frequency domain using Fast Fourier Transform (FFT). A temporal sample of the measured signal surrounding a target movement is cut out and its frequency content is analyzed. Typically, an impaired driver has rather low gain, and thus the frequency content of smooth pursuits and catch-up saccades is mainly in the lower frequencies. An unimpaired driver will have a higher high-frequency content.

Another way to determine Eye Movement Gain is to perform FFT analysis of gaze and target at the target's fundamental frequency. An unimpaired driver with a high gain would have a gaze frequency content close to the fundamental frequency of the target, while an impaired driver would have a more spread out content.

Figure 4:
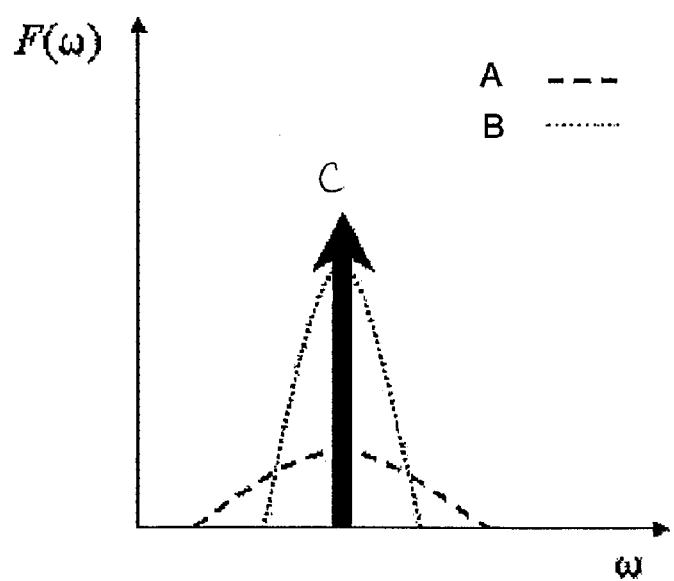
FIG. 4 shows curves in the frequency domain of the gain for impaired and unimpaired persons.

FIG. 4 shows the difference in gain for an impaired driver (curve A) relative to an unimpaired driver (curve B) when analyzed in the frequency domain relative to the fundamental frequency of the stimuli, which is represented by the arrow.

c) Perceptual impairment decision making:

After having quantified a value of perceptual suitability from at least one of the above indicators and weighting factors, a decision has to be made whether or not a driver is actually impaired (and, e.g., not able to drive a vehicle).

Decision-making is preferably conducted in two steps. In a first step, a short classification is done with an average target complexity. The stimulus is presented for a predetermined time, and the head/eye-tracking device 2/21 collects data. The indicators can be calculated on-line, i.e. during measurement, or off-line after the measurement. Each indicator is preferably normalized to a performance value between 0 and 100, where 100 represents good performance, and then weighted together according to the equation for the PS function above. The result is compared to thresholds either set specifically for every driver or predetermined by tests and statistical analysis of the PS function. Performance thresholds could also be set for each indicator, thus transforming the PS function into a combinatorial logic expression. If the driver response to the stimuli is sufficient, the test is negative and the driver is not impaired.

If there is any uncertainty in the result (i.e., there is suspicion of impairment), classification moves into a second step. In the second step, a longer test is performed (perhaps for several minutes) until a sufficient amount of data is collected by the system. The second step includes more complex tracking tasks, and the stimuli describe patterns that are of particular interest for the indicators that are uncertain. For example, a specific pattern may be executed by the stimuli to obtain relevant data for the SP Performance measure if the SP performance was in a grey zone (not sufficiently good or bad to make a decision) during the first step of decision-making.

During the second step, stimuli patterns change in speed, frequency, modulation, predictability, and direction. The more complex a pattern becomes, the more errors would be detected for an impaired driver.

An alternative embodiment to using the two-step approach above is to base calculation and stimulus generation on a moving time window approach. For example, a one minute time window can be used in a 60 Hz system (the moving time window thus includes 60 data samples in its window). During the first 60 data samples, the system generates stimuli of average complexity. At data sample number 60, the system calculates its decision on perceptual suitability. If the driver is not impaired, then he is allowed to drive. If the system finds the driver to be impaired or if it is suspicious, another stimuli sample is presented and a new calculation is performed on the window data plus the current data sample but also minus the oldest data sample (according to the use of a moving or running time window as is well known to those skilled in the art of signal processing).

This moving window-based presentation and calculation process continues until the driver passes the perceptual suitability test. If no time limit is imposed, an impaired driver can continue the test until the driver becomes unimpaired with time as the drug or alcohol effects wear off. Stimulus difficulty can be increased with time, making it more certain that a driver that previously has been tested as suspicious or impaired is currently unimpaired.

d) Output runs on the computation, control, and output device 3:

The driver opens his vehicle, sits down, and turns on the ignition. If so configured, the motor will not start until the Perceptual Suitability Test is passed. In another configuration, the motor starts but the vehicle is prevented from moving (this may be preferable for truck drivers). The main point is that the vehicle is prevented from moving until the driver has proven that he is perceptually suitable to drive.

The system is turned on when the key is put into the ignition. An indication light showing "Testing" is turned on. The driver would be required simply to watch a stimulus generated by the stimulus generation device 1/27. The idea is to present whatever stimulus is most effective in getting the driver to elicit the type of eye movement behavior being tested. Stimuli resembling what has been used in research can be used and further developed to meet the current needs.

The output can be sent to the vehicle-immobilizer (e.g., a part of the vehicle ignition 24) to enable it; be logged on a tachograph 25; or be transmitted by means of a communication device 26. Input to the computation, control, and output device 20/3 could be managed through a number of conventional ways. Various buttons and controls 23 could be mounted on the device 20/3, wherein communication cables or wireless communication could be used.

To ensure that the driver himself/herself is conducting the test, the system can be used together with driver identification software such as facial recognition or iris recognition systems.

Use While Driving:

Importantly, a system according to the invention can be used during driving or during the use of other equipment to continuously test for perceptual impairment of the driver. Detection of perceptual impairment from natural eye movements during driving is entirely possible. For example, current eye and head movements while driving can be compared to descriptions or thresholds describing impaired perceptual behavior. An alteration in eye movements because of alcohol, drugs, and medical conditions is established in literature. For example, Belt (1969) found a significant concentration of eye movement patterns or spatial gaze concentration at a blood alcohol content level of 0.08 mg/cm3. Drivers may exhibit more "foveal compensation" for loss of peripheral vision, that is, drivers may increasingly look at the lane markings on both sides close to the vehicle when perceptually impaired, presumably because they have lost sensitivity in peripheral vision. One might find that the frequency of smooth pursuits is significantly reduced. According to the invention, it is proposed to perform this classification on-line.

Another possibility if degradation in natural eye movements is noted is to trigger a presentation of certain stimuli to further test if a driver is impaired and ensure that the correct classification is or has been made. Thus, the stimulus generation device 1/27 could be used to produce stimuli also while driving. Great care will have to be taken to ensure the stimuli will not interfere with driving. However, if degradation in natural eye movement is detected, then warnings can be given, the event can be logged, the event can be transmitted to another source, the vehicle can be stopped, etc.

An alternate functionality instead of testing the ability of the driver to drive before driving, as is done with ignition interlocks, is to allow the driver to start the vehicle and start driving, but to require him/her to pass a test that is administered while driving in the first minutes, or continuously throughout the entire drive, or randomly during the drive. This represents a less severe inconvenience to the driver, but it would stop the vehicle or cut off the gas, etc., if impairment was detected.

Figure 5:
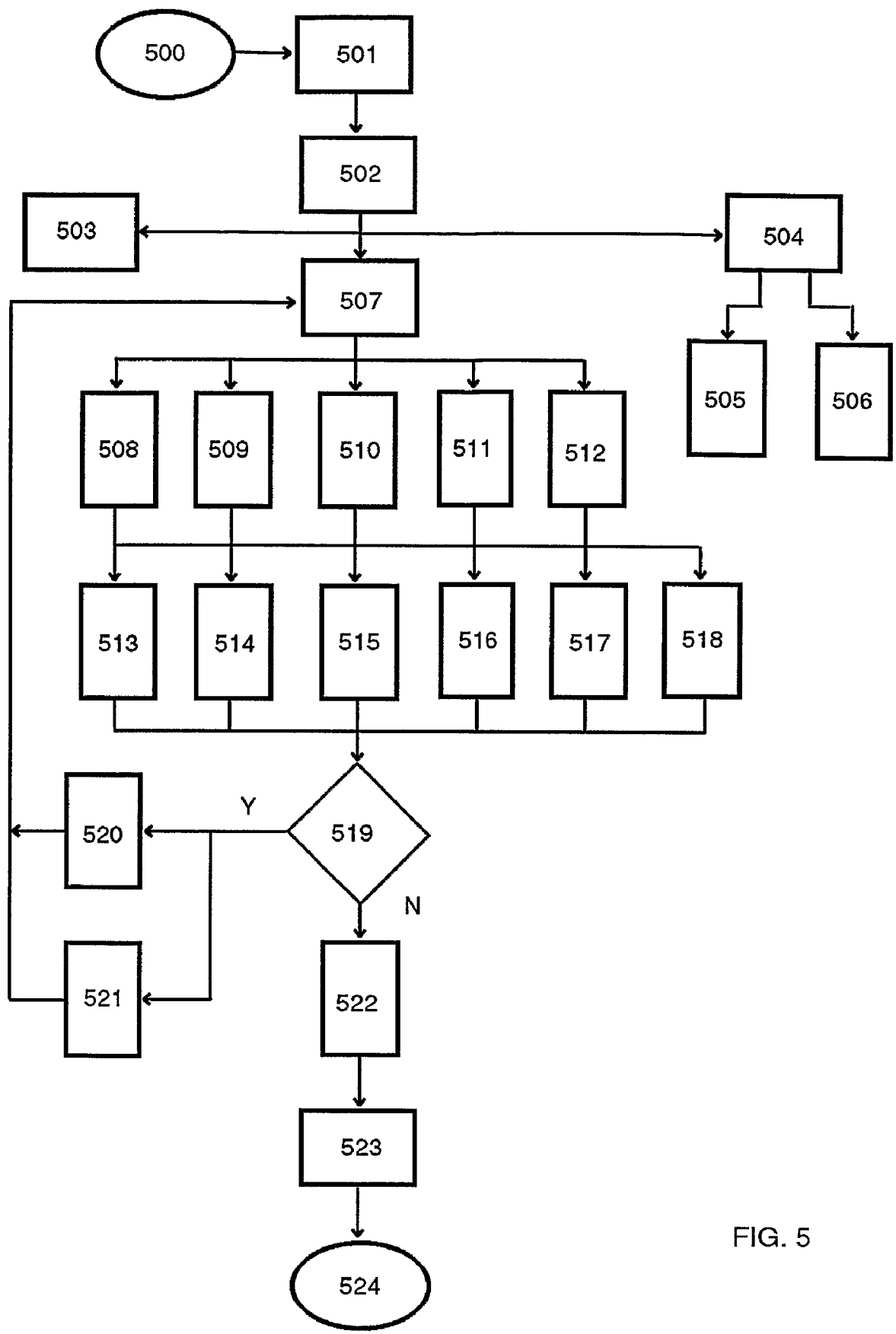
FIG. 5 shows a first part of a flowchart of a method for conducting a perceptual suitability test of a person according to the invention.
Figure 6:
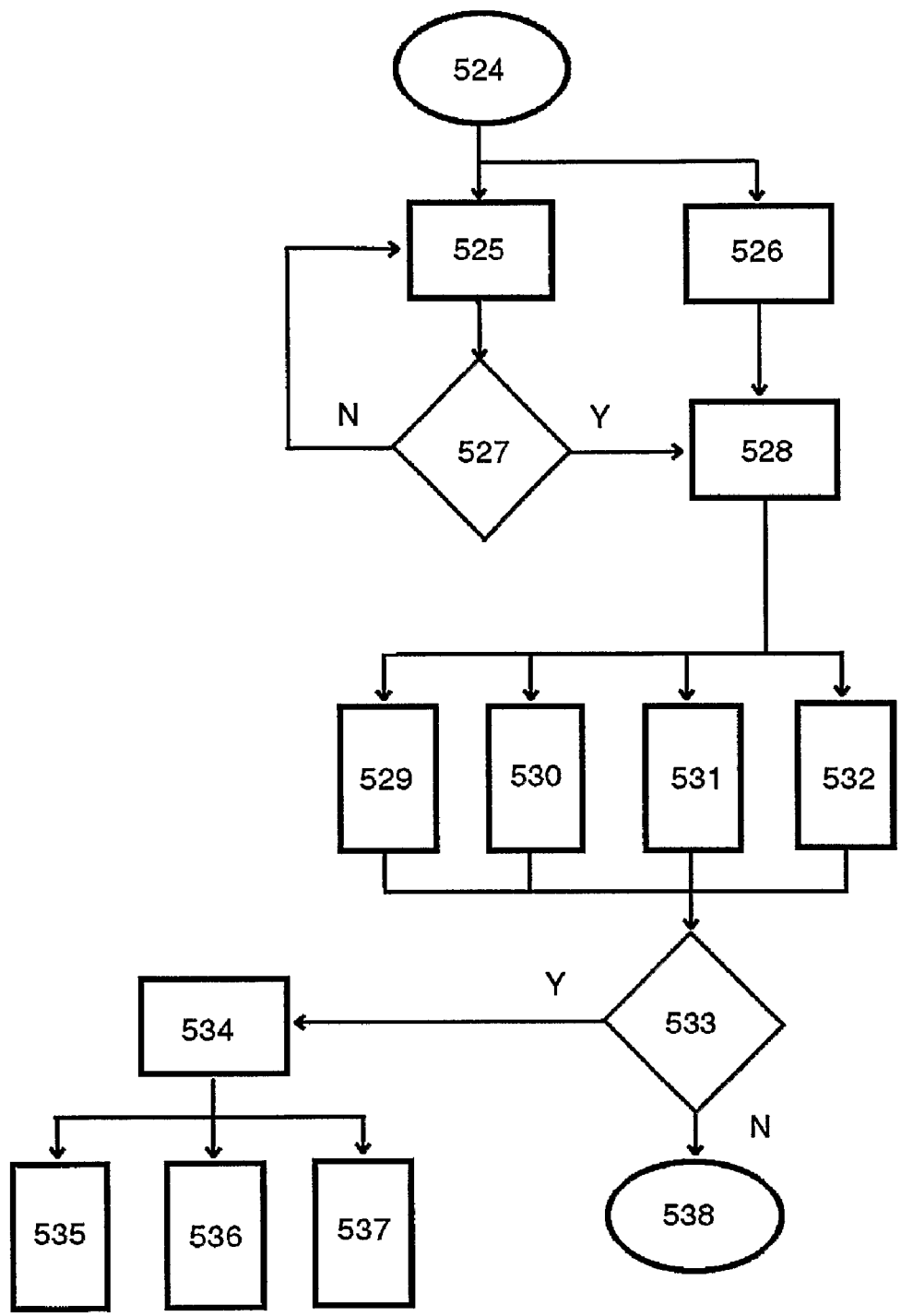
FIG. 6 shows a second part of the flowchart that begins in FIG. 5.

FIGS. 5 and 6 show a preferred embodiment of such a method which is conducted by a system according to the invention.

After a driver has entered the vehicle and has turned the ignition key, the method is started with step 500. In step 501, an immobilizer or an ignition interlock switch is activated. In step 502, a starting and power-up test routine is conducted. If this has been passed successfully, a display status testing is conducted in step 503. Furthermore, a stimuli generation device is activated in step 507.

Optionally, a bypass test is conducted with step 504 by pressing a button, by which either a bypass event is logged to a tachograph with step 505 and/or a message is sent (for example, to a fleet management system or an external source) in step 506. By means of the stimulus generation device, in at least one of steps 508 to 512, smooth pursuit stimuli, pupil reaction stimuli, head coordination stimuli, vergence stimuli and/or saccade/visual event stimuli are generated.

At least one of the above-explained performance ocular indicators is then quantified or calculated from the detected reactions of the driver as mentioned above. More particularly, in at least one of steps 513 to 518, smooth pursuit performance, pupil reaction performance, head coordination performance, vergence performance, saccade performance and/or other ocular performance indicators are calculated.

Then in step 519, the perceptual suitability of the driver is quantified (calculated) by a weighed combination of these indicators according to the formula PS given above, and it is decided from the quantified value whether the driver has to be considered impaired or not.

If the driver is not impaired, a related status indication "test passed" is displayed according to step 522, and the immobilizer and/or the ignition interlock switch is deactivated in step 523. The method is then continued with step 524 according to FIG. 6.

If it is detected in step 519 that the driver has to be considered as impaired or if it is uncertain that he is not impaired, a related status indication "test failed" is displayed in step 520. Furthermore, in step 521, a test with an increased stimulus difficulty is activated and conducted as explained above, and the routine is continued and conducted again with step 507 for generating such stimuli.

According to step 525, at least one of the ocular performance indicators of the driver is monitored during driving. In step 527, these indicators are tested for significant changes (for example, by comparing with predetermined thresholds).

If there are no significant changes, the procedure is continued with step 525. If significant changes occur, at least one stimulus is generated in step 528. Independent from this, the stimulus generation can be activated by means of step 526 at random time intervals.

Corresponding with steps 508 to 512, a stimulus for at least one ocular performance indicator is generated, and from the reaction of the driver the related indicator performance is calculated or quantified with at least one of steps 529 to 532. More particularly, these indicators are again smooth pursuit performance, head coordination performance, pupil reaction performance, and/or saccade performance.

As in step 519, in step 533, again the perceptual suitability of the driver is quantified (calculated) by a weighted combination of these indicators, and it is decided from the quantified value whether the driver has to be considered as impaired or not. If the driver is not impaired, the method is continued with step 538 which is continued with step 524.

If it is detected in step 533 that the driver is impaired, or if it is uncertain that he is not impaired, appropriate countermeasures are initiated in step 534. For example, these countermeasures can comprise sending a message to an external unit (step 535) and/or indicating a warning signal to the driver (step 536) and/or shutting down the vehicle (step 537).

What is claimed is:

1. A method for automatically executing a suitability test with respect to perceptual impairment of a driver or other equipment operator, comprising the steps of:
   (a) presenting at least one first optical stimulus pattern to the equipment operator;
   (b) detecting and quantifying at least one ocular performance indicator of the equipment operator selected from the group consisting of smooth pursuit (SP), saccadic velocity (SV), vergence (V), pupil reaction (PR), and head coordination (HC) in response to the stimulus;
   (c) quantifying a value of perceptual suitability (PS) of the equipment operator by the formula:

$$PS = A*SP + B*PR + C*HC + D*V + E*SV,$$

wherein A, B, C, D, and E are predetermined weighting factors or functions;
   (d) comparing the value of perceptual suitability (PS) with at least one threshold value in order to generate a decision about impairment or non-impairment of the equipment operator, and
   (e) if there is uncertainty in the result of said comparing or suspicion of impairment, presenting at least one second optical stimulus pattern with a greater complexity than the at least one first optical stimulus pattern and/or presenting at least one second optical stimulus pattern which is germane to the ocular performance indicator which is uncertain under step (d), and repeating steps (b) to (d) therewith.

2. The method according to claim 1, where said method is executed automatically with predetermined time intervals at the start and/or during operation of the equipment.

3. The method according to claim 1, wherein.
   (a1) a moving or running time window is provided, during which step (a) is performed;
   (b1) at the end of the time window, step (d) is performed, and
   (c1) step (e) and the repetition of steps (b) to (d) are performed on the window data samples including the current data sample but excluding the oldest data sample of said window data samples according to a moving or running time window approach.

4. The method according to claim 1, wherein the at least one second optical stimulus pattern is presented for a longer time than the at least one first optical stimulus pattern is presented.

5. The method according to claim 1, wherein the at least one second optical stimulus pattern changes in speed, frequency, modulation, predictability, and/or direction.

6. The method according to claim 1, wherein the at least one first optical stimulus pattern is presented to the equipment operator by projecting the pattern by means of a diode laser.

7. The method according to claim 1, wherein for each ocular performance indicator a threshold is set.

8. The method according to claim 1, wherein the weighting factors or functions are chosen in order to minimize influences of a given installation of a system for conducting the method and/or an environmental state and/or other conditions which influence the result of the quantification of the perceptual suitability (PS).

9. The method according to claim 1, wherein the weighting factors or functions are tuned during or between repeated executions of the method.

10. The method according to claim 9, wherein the weighting factors or functions are tuned by neural networks and/or in dependence on an analysis of the performance indicators and/or a noise content in detected values of the indicators and/or indicator confidence.

11. The method according to claim 1, wherein the degree of difficulty for the equipment operator in tracking a stimulus in order to detect the smooth pursuit performance indicator is varied.

12. The method according to claim 1, wherein a stimulus presented to the equipment operator in order to detect the smooth pursuit performance indicator is varied in its degree of predictability by changing the combination of numerous sinusoids and/or a low-pass Gaussian random process and/or by stopping the stimulus randomly in the periphery of the visual field of the driver.

13. The method according to claim 1, wherein at least one of the ocular performance indicators is calculated using angular RMS values.

14. The method according to claim 1, wherein at least one of the ocular performance indicators is calculated by cross correlations between gaze directions and predefined motions of the eyes of the equipment operator which are common in natural driving.

15. The method according to claim 1, wherein at least one of the ocular performance indicators is calculated using a general model response.

16. The method according to claim 1, wherein at least one of the ocular performance indicators is calculated using a trained model response in which the model is linked to the identity of the equipment operator.

17. The method according to claim 1, wherein in order to detect the performance indicator of pupil reaction ambient light is compensated.

18. The method according to claim 1, wherein a peripheral sensitivity of the equipment operator is analyzed using performance indicators of saccadic velocity and/or pupil reaction in response to sudden visual events which are triggered at various visual angles.

19. A system for automatically executing a suitability test with respect to perceptual impairment of a driver or any other person who operates a piece of equipment and/or device for conducting a method according to claim 1 and comprising a stimulus generation device (1), an eye movement and/or head movement and/or pupil reaction registration device (2) and a computation, control and output device (3) for controlling the stimulus generated by means of the stimulus generation device (1), for classification of the eye/head movement, pupil reaction data detected by the eye/head movement/pupil reaction registration device (2) and for perceptual impairment decision making.

20. Equipment and/or device the operation of which could especially pose a general and/or potential risk for the environment and/or other people, comprising a system according to claim 19.

21. A computer program comprising computer program code means adapted to perform a method according to claim 1 when said program is run on a programmable microcomputer.

22. A computer program according to claim 21, when run on a computer which is connected to the internet, is adapted to be downloaded to a system or one of its components for automatically executing the suitability test with respect to perceptual impairment of a driver or any other person who operates a piece of equipment and/or device and comprising a stimulus generation device (1), an eye movement and/or bead movement and/or pupil reaction registration device (2) and a computation, control and output device (3) for controlling the stimulus generated by means of the stimulus generation device (1), for classification of the eye/head movement, pupil reaction data detected by the eye/head movement/pupil reaction registration device (2) and for perceptual impairment decision making.

23. A computer program product stored on a computer readable medium, comprising computer program code means according to claim 21.

24. The Equipment and/or device according to claim 20 wherein said equipment and/or device is selected from the group consisting of a vehicle, train, aircraft, ship, nuclear reactor, plant, or a chemical process.

* * * * *